United States Patent
Denninghoff

(10) Patent No.: US 6,390,989 B1
(45) Date of Patent: May 21, 2002

(54) OXIMETRIC TONOMETER WITH INTRACRANIAL PRESSURE MONITORING CAPABILITY

(75) Inventor: Kurt R. Denninghoff, Vestavia, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/720,022

(22) Filed: Feb. 27, 2001

Related U.S. Application Data

(60) Provisional application No. 60/089,856, filed on Jun. 19, 1998.

(51) Int. Cl.[7] .............................................. A61B 05/00
(52) U.S. Cl. ........................................................ 600/561
(58) Field of Search .......................................... 600/561

(56) References Cited

U.S. PATENT DOCUMENTS

| | | | | |
|---|---|---|---|---|
| 3,929,124 A | * | 12/1975 | Yablonski et al. | 600/310 |
| 5,987,351 A | * | 11/1999 | Borchert et al. | 600/473 |
| 6,086,533 A | * | 7/2000 | Madsen et al. | 600/561 |
| 6,129,682 A | * | 10/2000 | Borchert et al. | 600/561 |

\* cited by examiner

*Primary Examiner*—Robert L. Nasser
(74) *Attorney, Agent, or Firm*—Gifford, Krass, Groh, Sprinkle, Anderson & Citkowski, P.C.

(57) ABSTRACT

A method is disclosed for non-invasive determination of intracranial pressure using an intracranial pressure monitor. The method preferably includes retinal scanning with a retinal scanner of the ocular fundus to determine dioxyhemoglobin saturation within the blood vessels of the retina. Through simultaneous monitoring of the cardiac cycle with a cardiac cycle monitor during retinal scanning and measurement of the intraocular pressure, intracranial pressure is determined independent of implanting or adhering the sensing device to the head or neck region of a test subject.

21 Claims, 2 Drawing Sheets

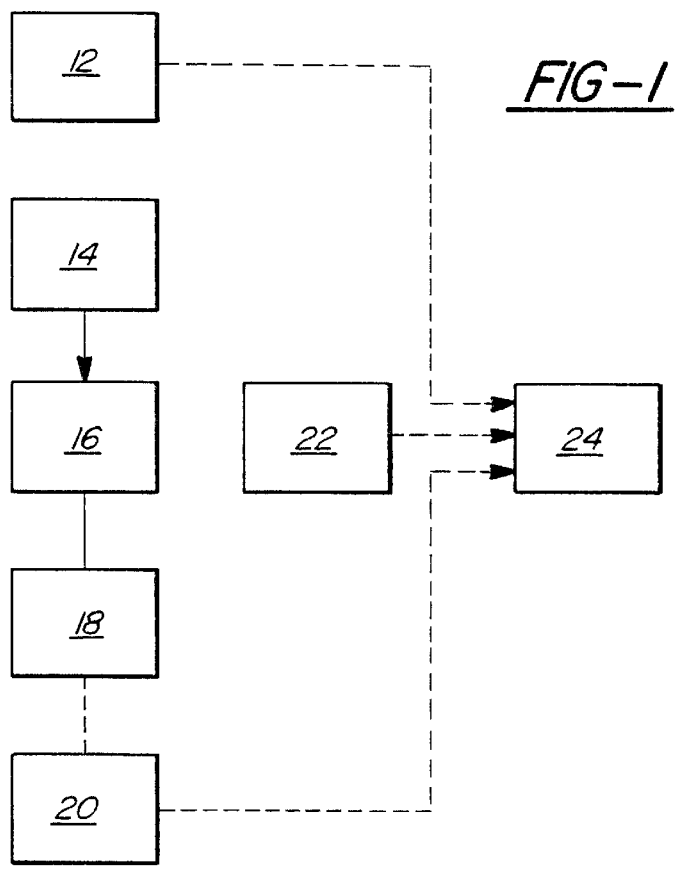
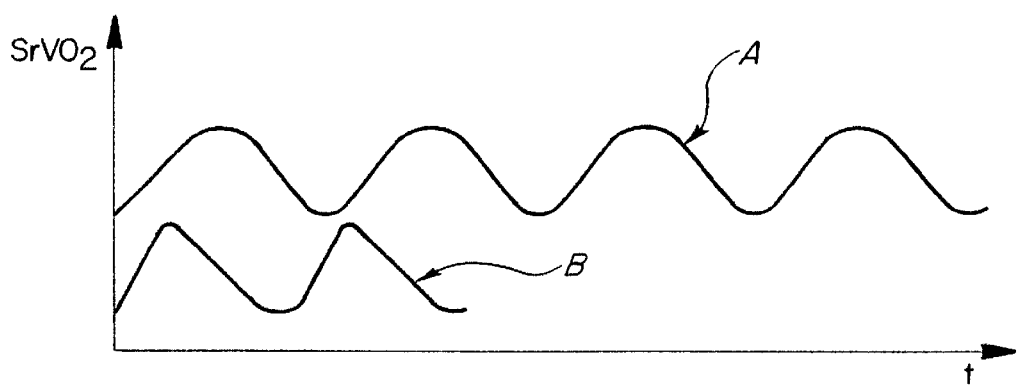

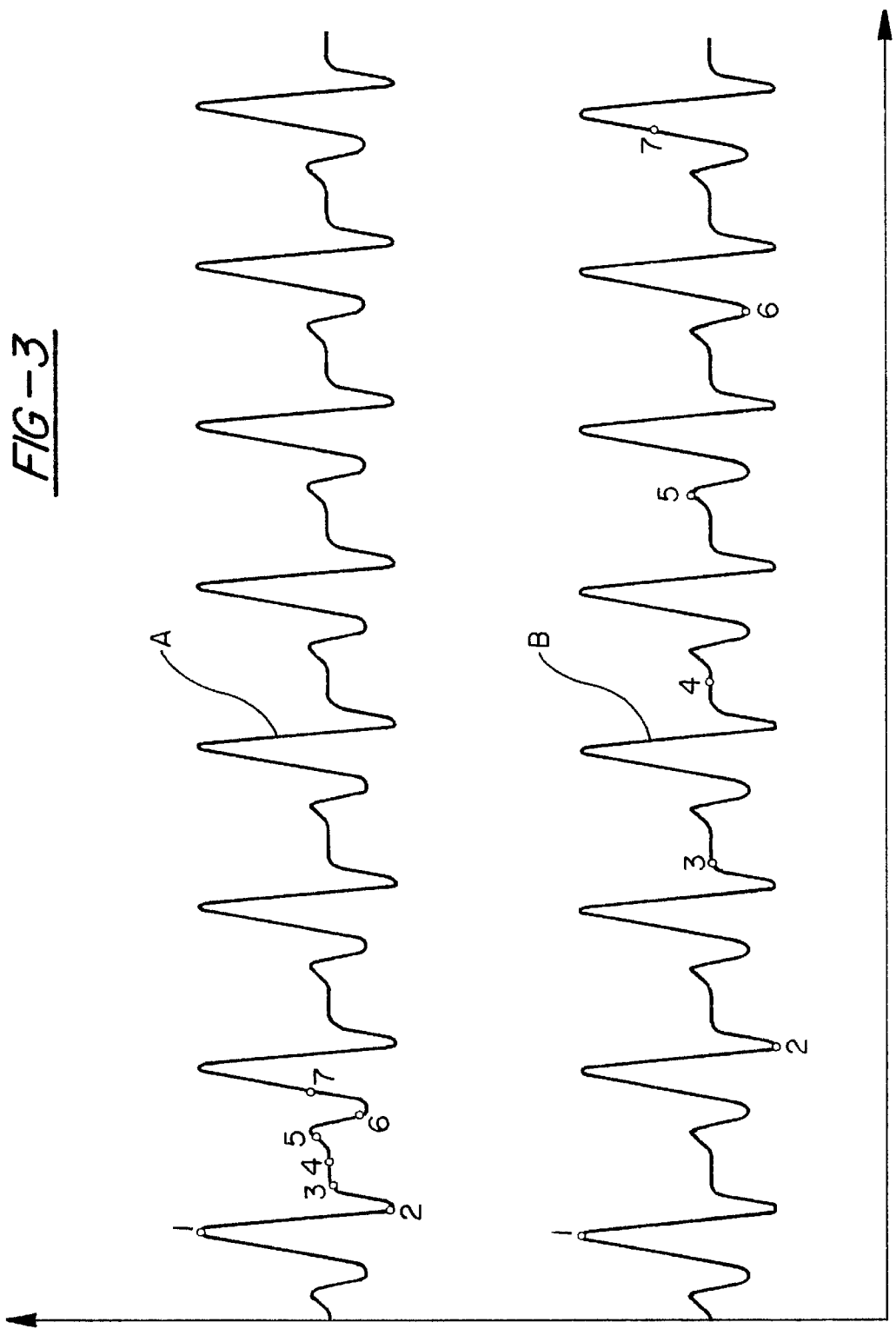

OXIMETRIC TONOMETER WITH INTRACRANIAL PRESSURE MONITORING CAPABILITY

RELATED APPLICATION

This patent application claims priority of provisional patent application 60/089,856, filed Jun. 19, 1998, entitled "Oximetric Tonometer with Intracranial Pressure Monitoring Capability."

FIELD OF THE INVENTION

This invention relates generally to non-invasive medical procedures and, in particular, to a method of analyzing retinal blood vessels to ascertain intracranial pressure non-invasively.

BACKGROUND OF THE INVENTION

Monitoring of intracranial pressure is a of diagnostic and postoperative value for medical treatment of injured or diseased patients. This is especially true of individuals who have suffered closed head injuries, hemorrhagic strokes hydrocephalics and neurosurgery patients. Individuals suffering from such conditions are prone to experience brain swelling, infections, hemorrhages, edema and obstruction of cerebrospinal fluid ducts. Through the monitoring of intracranial pressure, potentially dangerous pressure changes can be relieved prior to attaining dangerous levels, and postoperative pressures can be monitored to assure a successful result or screening diagnostics can be performed which are indicative of such conditions.

Traditionally, intracranial pressure has been measured by insertion of a calibrated needle with pressure monitored as a function of the height a column of fluid rises within the needle as measured in millimeters mercury. While this method is both simple and direct, the invasiveness and discomfort associated with direct monitoring of intracranial pressure has led the art to explore non-invasive methods for monitoring intracranial pressure.

Non-invasive methods for monitoring intracranial pressure have taken advantage of various relationships between other physiological characteristics and intracranial pressure. For instance, measurement of a pressure volume index using ultrasonic blood flow transducers as described in U.S. Pat. No. 5,617,873; measurement of blood flow within the jugular vein following occlusion therein, as described in U.S. Pat. No. 4,204,547; measuring brain activity in response to sensory stimulus, as described in U.S. Pat. No. 4,564,022; pneumatic tonometry measurements, as described in *Am. J. Dis. Child* 137 (1983): 332; ultrasonic pulse probing, as described in U.S. Pat. No. 4,984,567; and listening to the skull cavity through the use of a microphone, as described in U.S. Pat. No. 4,008,711. While the relative merits of these various non-invasive approaches remains unsettled, a common feature of prior art methods for monitoring intracranial pressure is the adhesion of some type of sensor to a subject. Further, the prior art methods typically favor a subject to remain stationary in a supine position to obtain satisfactory measurements of intracranial pressure. Thus, a subject remains tethered to intracranial monitoring equipment necessitating a separate monitoring device for each subject. Thus, there exists a need for a method measuring intracranial pressure that does not require the adhesion of sensors to a subject, so as to facilitate periodic multiple subject monitoring with a single intracranial pressure monitoring device.

Normally, venous hemoglobin is 75 percent saturated with oxygen, thereby providing a reserve for critical states such as hemorrhage or heart attack, when more oxygen must be extracted by body organs. As a consequence, during bleeding states, capillary red blood cells upload more oxygen into tissues, resulting in a lower post-capillary venous oxygen saturation which may be detected and-used to assess the rate and quantity of internal hemorrhage over time.

Although the level of desaturated hemoglobin may be assessed invasively, as with catheters inserted into the subclavian vein or forearm vein, non-invasive procedures are preferred to minimize stress and infection. One such non-invasive technique is disclosed in U.S. Pat. No. 5,119,814, wherein a method and apparatus for monitoring blood loss via retinal venous oxygen saturation is provided to detect changes in the oxygen saturation of the retinal veins when internal bleeding in a patient occurs. The apparatus includes a retinal scanner that illuminates a plurality of points on the fundus and detects reflectance, and a signal processing means that uses reflectance spectroscopy techniques to convert the reflected signals into data points that can be stored or displayed. A decline in the value of these data points indicates a drop in venous hemoglobin saturation that allows the user to determine the rate and estimate the volume of blood loss.

Improvements to the system just described are disclosed in U.S. Pat. No. 5,308,919, wherein the optic disk region of the ocular fundus is illuminated with three or more wavelengths of light focused in approximately the same area. One of the light sources serves as a tracking beam which, through reflectance spectroscopy is used to determine when the tracking light beam is focused upon the optic disk. The scanning light beams are primarily focused within the boundary of the tracking beam. The intensity of light reflected from retinal venous and arterioles is detected, and the arteriole venous oxygen difference is determined.

Spectroscopic interrogation of the ocular fundus is known to the art to be a non-contacting method of obtaining vascular and ophthamologic information. For example, blood vessel dimensions and metering information is obtained through illumination of the fundus, as described in U.S. Pats. No. 5,090,799; 5,640,963 and 4,950,070. The prior art has heretofore not determined whether intracranial pressure is related to the flow characteristics of blood vessels within the ocular fundus.

SUMMARY OF THE INVENTION

The present invention provides a method for estimating intracranial pressure by the measurement of deoxyhemoglobin saturation obtained through retina scanning. A method of the present invention includes measuring a subject cardiac cycle while impinging with a light beam on a blood vessel within a subject retina. The light beam is used to measure physical characteristics of the blood vessel to determine subject deoxyhemoglobin saturation. Based on measurement of a subject intraocular pressure, cardiac cycle and the deoxyhemoglobin saturation, intracranial pressure is calculated. The method of the present invention is contrasted with prior art methods of non-invasively determining intracranial pressure in that scanning a subject retina while simultaneously measuring the subject cardiac cycle occurs independently of implanting or adhering a sensing device to a subject head or neck region. The determination of intracranial pressure based upon deoxyhemoglobin saturation within blood vessels of the retina is a novel aspect of the present invention. Other aspects and advantages will become apparent hereinafter.

BRIEF DESCRIPTION OF THE DRAWINGS

FIG. 1 is a schematic block diagram of the measurement process steps according to an embodiment of the present invention with solid lines, corresponding to process steps and dashed lines corresponding to computational steps.

FIG. 2 shows the venous oxyhemoglobin saturation ($SrVO_2$) as a function of time where the oscillatory period corresponds to a cardiac cycle (A) with normal intracranial pressure and (B) with elevated intracranial pressure.

FIG. 3 shows different acquisition profiles sampling sequences according to the present invention across the time interval of the cardiac cycle.

DETAILED DESCRIPTION OF THE PREFERRED EMBODIMENTS

The present invention recognizes the phenomenon that increased intracranial pressure causes a decrease in arterial blood flow to the brain as blood vessels become compressed. The present invention utilizes the discovery that increased intracranial pressure causes a reduction in blood flow to the retina. This reduction in blood flow to the retina, in turn, results in a change in arterial and venous blood-vessel diameter is observable as attenuation of retinal vessel pulsation. Thus, the cardiac-cycle waveforms are altered. Assuming that a blood vessel easily dilates and is flexible without obstructions, the rising edge of the cardiac waveform associated with each cardiac cycle tends to deflect sharply. In contrast, a rising edge of the cardiac waveform having a lesser deflection slope is indicative of an obstruction or compression of the vessels as the pulsalitile blood flow is hindered from expanding vessel walls.

In a clinical setting, the present invention has utility in screening subjects complaining of headache pain. Through a retinal scan to determine if vessel pulsation has been attenuated, the elevation of intracranial pressure becomes apparent indicating a condition requiring intervention or further monitoring. Additionally, intraocular pressure measured according to the present invention is clinically significant in screening for ocular pressure related diseases such as glaucoma.

Increased intraocular pressure usually results from incomplete flushing of the intraocular fluid, which may compress the vessels at the back of the eye and damage the nerves in severe cases. Most normal subjects, i.e. those with normal intracranial pressure, have prominent venous pulsations at the optic disc. In 20% of normal individuals, retinal venous pulsations are not visible to the observer. In this group, the pulsations are still present, albeit attenuated and thus undetectable with simple observation. It is an object of the present invention to enable instrument detection of attenuated venous pulsations in normal subjects. When coupled with oximetric techniques, it is found that these normal variants maintain their retinal venous oxygen saturation in the normal range, assuming no co-existent disease state which might alter retinal oxygen saturation.

It is a further object of this invention to detect attenuated or absent venous pulsations during rising intracranial pressure. These subjects concurrently display a fall in the retinal venous oxygen saturation. This is also seen with increasing intraocular pressure, thus necessitating the acquisition of a baseline intraocular pressure measurement.

It is yet a further object of the present invention to monitor the restoration of retinal venous pulsations as well as oxygen saturation to normal with treatment of intracranial hypertension. According to one aspect of this invention, intraocular pressure is measured to obtain a baseline with respect to the size of the retinal vessels to ensure that any compression, if present, is not due to intraocular pressure. Once this baseline is obtained, it may be assumed that any changes in waveform are due to problems associated with intracranial pressure.

Changes in deoxyhemoglobin saturation are more pronounced with increased intraocular and/or increased intracranial pressure due to the fact that as circulation slows, more oxygen is extracted from the vessels in any given cardiac cycle Due to the reduction in blood flow, the amount of oxygen saturation in the venous side is reduced, because a greater percentage of the oxygen has been released into the body tissue.

The present invention improves upon, and further extends, the concept of non-invasive monitoring of the arterial/venous oxygen difference from the ocular fundus by measuring changes in perfusion of the eye during the cardiac cycle. In particular, the present invention uses eye oximetry to monitor changes in intraocular and/or intracranial pressure by measuring changes in the retinal arterial/venous deoxyhemoglobin saturation ($SrVO_2$) preferably using the cardiac cycle as a reference. The present invention operates on the discovery that a decrease in $SrVO_2$ occurs with increased intraocular pressure and/or increased intracranial pressure. Upon measurement of intraocular pressure to obtain a dimensional baseline as to retinal vessels, any variations in $SrVO_2$ are attributable to intracranial pressure changes. It is appreciated that intraocular pressure measurements are optionally compiled in tabular form from a dimensional range of retinal vessels and intraocular pressures, including pressures obtained by conventional methods common to the detection and monitoring of glaucoma. Such tabular data can provide an independent basis for determining intraocular pressure. In all cases, measuring intracranial pressure does not involve contacting the subject, and is non-invasive.

Sample Protocol for Usage of the Retinal Intracranial Pressure Monitor

Direct Pressure Measurement

In reference to FIG. 1, intraocular pressure is measured in the subject or determined from tabular data based upon the ocular field interrogated prior to the intracranial pressure measurement 12. Thereafter, a target device (or direct visualization by the operator), aims the retinal intracranial pressure monitor (RICP) at a large vessel in the area of the optic nerve head 14. A laser scan of the blood vessels in this area about the optic nerve head is made 16. The laser scan is used to measure the vessel characteristics 18 such as diameter/shape and thereby obtain deoxyhemoglobin saturation of the blood in each vessel over the duration of the scan 20.

Each laser scan preferably is performed in less than 80 milliseconds, with repeated scans being taken over several cardiac cycles. The subject electrocardiogram (EKG) is simultaneously monitored during scanning 22 and the scan parameters correlated with the cardiac cycle events. The data obtained from the RICP is analyzed to identify the waveform characteristics associated with a particular intracranial pressure level 24. The input data for determining intracranial pressure includes the intraocular pressure, the EKG, and the processed signal from the RICP. It is appreciated that qualitative intracranial pressure is estimated independent of EKG or intraocular pressure data.

The relationships between intraocular pressure, $SrVO_2$ and cardiac cycle information used to determine intracranial pressure are readily modeled with a variety of mathematical formulae. The relationship between the parameters is analyzed in different ways with respect to the particulars of measuring $SrVO_2$. Factors considered in determining the, relationship include scan time, vessel dimensions and shape, uniformity of pressure application about the vessel and the like. Generally, it is appreciated that intraocular pressure is related to an inverse power of blood flow. Intracranial pressure is also related to an inverse power of blood flow. Blood flow is measured as an experimental value from the EKG cardiac cycle measurement and retinal vessel dynamic physical measurement obtained from the RICP. $SrVO_2$ is related to an absolute value power of blood flow. It is appreciated that in addition to $SrVO_2$, retinal arterial/venous carboxyhemoglobin saturation $SrVCO_2$ measurement is also operative in the present invention wherein the summation of deoxyhemoglobin and carboxyhemoglobin is equal to the total hemoglobin content. Thus, by determining the intraocular pressure and $SrVO_2$ within a known temporal phase of the cardiac cycle, intracranial pressure becomes proportional to a power of intraocular pressure inversely proportional to a power of blood flow and inversely proportional to a power of $SrVO_2$. Preferably, intracranial pressure is computed by a microprocessor loaded with a computer program. The intracranial pressure thereafter being displayed to a device operator.

Relative Pressure Measurement

The RICP is used optionally as described above over time with the change in pressure being recorded over time, thereby allowing the operator to detect relative changes in intracranial pressure. Dynamic changes in intracranial pressure allow a clinician to identify patients with increasing or decreasing intracranial pressure. This is important since increases in pressure of less than 10 mmHg above the normal 40 mmHg intracranial pressure is sufficient to cause brain damage. The waveform of FIG. 2A shows a venous deoxyhemoglobin saturation wave without increased intracranial pressure, whereas FIG. 2B depicts a venous deoxyhemoglobin saturation wave with increased pressure over the same time.

Sample Protocol for Usage of the Retinal Intraocular Pressure Monitor

In patients without increased intracranial pressure, a target device or direct visualization by the operator is used to aim the retinal intraocular pressure monitor (RIOP) at a large vessel in the area of the optic nerve head. A laser scan of a blood vessel in this area is used to measure the vessel diameter/shape and the oxygen saturation of the blood in each vessel. Each scan is performed in less than 80 milliseconds, with repeated scans being taken over several cardiac cycles. The EKG is simultaneously monitored, and the changes in the measured parameters during the cardiac cycle are recorded. The data obtained from the RIOP is analyzed and processed, using as input the EKG cardiac cycle data and the processed signal from the RIOP. The values thereof being related as detailed above. The waveform characteristics associated with a particular intraocular pressure level are identified and then displayed to a device operator and input into intracranial pressure calculation.

Instrumentation

Instrumentation is required for acquiring vessel absorption profiles temporally across the cardiac cycle.

There are at least two ways to acquire retinal vessel absorption profiles. A scanning system is optionally, used. Scanning laser ophthalmoscopes and the eye oximeter represent systems of this type. The apparatii detailed in U.S. Pat. Nos. 5,308,919 and 5,640,963 are representative of instruments for acquiring vessel absorption profiles according to the present invention. The second technique involves a retinal imaging system. Systems of this type include fundus cameras and retinal microscopes. The apparatii detailed in U.S. Pat. Nos. 4,423,931; 4,402,601 and 5,233,517 are representative of retinal imaging instruments for acquiring vessel absorption profiles according to the present invention. Using either technique, retinal vessel absorption profiles are acquired similar to the ones illustrated in FIG. 1.

The next step is to acquire these profiles at different times along the cardiac cycle. There are at least two ways of doing so. These methods are illustrated in FIG. 3. The first method is to acquire retinal vessel absorption profiles to obtain $SrVO_2$ rapidly in succession with a single cardiac cycle. This technique is illustrated in FIG. 3A. This method is the preferred embodiment. Another method for acquiring these scans is to build up a temporal profile by including scans acquired at different points across multiple cardiac cycles. This method is illustrated in FIG. 3B.

The foregoing is considered as illustrative only of the principles of the present invention. Numerous modifications and changes will be readily apparent to those skilled in the art without departing from the spirit of the invention, and accordingly all suitable modifications and equivalents leading thereto are intended to fall within the scope of the invention as claimed.

All references cited herein are intended to be incorporated by reference to the full extent as if each individual reference was individually and specifically incorporated by reference.

What is claimed is:

1. A non-invasive method of determining intracranial pressure comprising the steps of:
   measuring a subject cardiac cycle;
   measuring a subject intraocular pressure;
   aiming a retinal intracranial pressure monitor at a blood vessel within a subject retina;
   impinging with a light beam on the blood vessel while measuring the subject cardiac cycle;
   measuring physical characteristics of the blood vessel to determine a subject deoxyhemoglobin saturation;
   calculating intracranial pressure from observable parameters comprising:
      the intraocular pressure, the cardiac cycle and the deoxyhemoglobin saturation.

2. The method of claim 1 wherein measuring the subject cardiac cycle comprises collecting a subject electrocardiogram.

3. The method of claim 1 wherein a targeting device serves to aim the retinal intracranial pressure monitor at the blood vessel.

4. The method of claim 1 wherein a scanning laser beam is the light impinging on the blood vessel.

5. The method of claim 4 wherein the laser beam scans the vessel for less than 80 milliseconds.

6. The method of claim 5 wherein a plurality of scans are made of the blood vessel.

7. The method of claim 6 wherein each of the plurality of laser scans is acquired successively within a single cardiac cycle.

8. The method of claim 6 wherein the plurality of scans are phase shifted relative to one another across multiple cardiac cycles.

9. The method of claim 1 wherein the blood vessel is located in the area about an optic nerve head of the subject retina.

10. The method of claim 1 wherein the blood vessel characteristics are selected from a group consisting of vessel diameter and vessel shape.

11. A method of determining intracranial pressure which comprises non-invasively interrogating retinal blood vessels with light while simultaneously measuring the subject cardiac cycle.

12. A device for carrying out the process of claim 11.

13. An improved method of non-invasively determining intracranial pressure wherein the improvement lies in: scanning a subject retina while simultaneously measuring a subject cardiac cycle independent of implanting or adhering a sensing device to a subject head or neck region.

14. The improved method of claim 13 further determining intracranial pressure from deoxyhemoglobin saturation within vessels of the retina.

15. A method for determining intracranial pressure which comprises the step of:

non-invasively interrogating a retinal blood vessel with light to yield deoxyhemoglobin saturation and blood vessel characteristics.

16. The method of claim 15 wherein the blood vessel characteristics are selected from a group consisting of vessel diameter and vessel pulsations.

17. A non-invasive method of determining intracranial pressure comprising the steps of:

impinging with a light beam on a blood vessel within a subject retina to yield a subject deoxyhemoglobin saturation; and estimating intracranial pressure from the deoxyhemoglobin saturation.

18. The method of claim 17 further comprising the step of:

measuring a subject cardiac cycle while impinging with the light beam on the blood vessel.

19. The method of claim 18 further comprising the step of:

calculating intracranial pressure from the subject cardiac cycle and intraocular pressure derived from measuring optically subject intraocular pressure from characteristics of the blood vessel.

20. The method of claim 17 further comprising the step of:

measuring optically subject intraocular pressure from characteristics of the blood vessel.

21. A device for measuring intracranial pressure of a subject comprising:

an optical oximeter adapted to scan a subject optic blood vessel to yield deoxyhemoglobin saturation;

a simultaneously coupled electrocardiogram such that said oximeter scan is related to a cardiac cycle phase of the subject; and a microprocessor for calculating intracranial pressure from deoxyhemoglobin saturation and the cardiac cycle phase.

\* \* \* \* \*

UNITED STATES PATENT AND TRADEMARK OFFICE
CERTIFICATE OF CORRECTION

PATENT NO.     : 6,390,989 B1
DATED          : May 21, 2002
INVENTOR(S)    : Kurt R. Denninghoff It is certified that error appears in the above-identified patent and that said Letters Patent is hereby corrected as shown below:

Title page,
Item [57], ABSTRACT,
Line 5, replace "dioxyhemoglobin" with -- deoxyhemoglobin --.
Line 6, after "saturation" insert -- venous pulsations --.

Column 1,
Line 7, before "FIELD OF THE INVENTION" insert:
            -- GRANT REFERENCE
      The U.S. Government has a nonexclusive, nontransferable, irrevocable paid-up license to practice or have practiced this invention for or on it's behalf as provided for by the terms of Contract DAMD 17-98-1-8007 awarded by the U.S. Department of the Army. --.
Line 18, after "is" delete "a".
Line 21, after "Strokes" insert -- , --.

Column 4,
Line 5, after "cycle" insert -- . --.
Line 64, after "the" delete ","

Column 5,
Line 58, after "optionally" delete ","

Column 6,
Line 63, replace "shape" with -- pulsations --.

UNITED STATES PATENT AND TRADEMARK OFFICE
CERTIFICATE OF CORRECTION

PATENT NO. : 6,390,989 B1
DATED : May 21, 2002
INVENTOR(S) : Kurt R. Denninghoff It is certified that error appears in the above-identified patent and that said Letters Patent is hereby corrected as shown below:

<u>Column 7,</u>
Line 2, replace "An improved" with -- A --.
Line 3, replace "wherein the improvement lies in" with -- comprising --.

Signed and Sealed this

Twenty-sixth Day of November, 2002

*Attest:*

*Attesting Officer*

JAMES E. ROGAN
*Director of the United States Patent and Trademark Office*